US00PP21148P2

(12) United States Plant Patent
Hartman

(10) Patent No.: US PP21,148 P2
(45) Date of Patent: Jul. 6, 2010

(54) ***CALADIUM* PLANT NAMED 'WHITE STAR'**

(50) Latin Name: *Caladium×hortulanum*
Varietal Denomination: White Star

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/321,741

(22) Filed: Jan. 23, 2009

(51) Int. Cl.
*A01H 5/00* (2006.01)

(52) U.S. Cl. ..... Plt./373
(58) Field of Classification Search ..... Plt./373
See application file for complete search history.

*Primary Examiner*—Kent L Bell
(74) *Attorney, Agent, or Firm*—C. A. Whealy

(57) ABSTRACT

A new and distinct cultivar of *Caladium* plant named 'White Star', characterized by its intermediate to tall plant habit; vigorous and dense growth habit; rapid growth rate; and strap-type leaves that are white to grey-green in color with pink to light pink-colored veins and dark green-colored borders.

4 Drawing Sheets

Botanical designation: *Caladium×hortulanum.*
Cultivar denomination: 'WHITE STAR'.

BACKGROUND OF THE INVENTION

The present invention relates to a new and distinct cultivar of *Caladium* plant, botanically known as *Caladium×hortulanum*, commercially referred to as a strap leaf-type *Caladium* and hereinafter referred to by the name 'White Star'.

The objective of the Inventor's breeding program is to create new *Caladium* cultivars that have uniform plant habit, exceptional performance and attractive foliage coloration.

The new *Caladium* plant originated from a cross-pollination made by the Inventor in April, 2002, in Lake Placid, Fla. of *Caladium×hortulanum* 'White Wing', not patented, as the female, or seed, parent with *Caladium×hortulanum* 'Gingerland', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by tuber divisions in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Star'. These characteristics in combination distinguish 'White Star' as a new and distinct cultivar of *Caladium:*

1. Intermediate to tall plant habit.
2. Vigorous and dense growth habit; rapid growth rate.
3. Strap-type leaves that are white to grey-green in color with pink to light pink-colored veins and dark green-colored borders.

Plants of the new *Caladium* differ from plants of the female parent, 'White Wing', in the following characteristics:

1. Plants of the new *Caladium* are not as upright as plants of 'White Wing'.
2. Plants of the new *Caladium* grow faster than plants of 'White Wing'.
3. Leaves of plants of the new *Caladium* are more rounded than and not as pointed as leaves of plants of 'White Wing'.
4. Plants of the new *Caladium* and 'White Wing' differ in leaf coloration as plants of 'White Wing' have white-colored leaves with a mottled dark and light green-colored borders.

Plants of the new *Caladium* differ primarily from plants of the male parent, 'Gingerland', in leaf coloration as plants of 'Gingerland' have white-colored leaves with red-colored spots and dark green-colored borders.

Plants of the new *Caladium* can be compared to plants of 'Mount Everest', not patented. In side-by-side comparisons conducted in Lake Placid, Fla., plants of the new *Caladium* differed primarily from plants of 'Mount Everest' in the following characteristics:

1. Plants of the new *Caladium* were more compact than plants of 'Mount Everest'.
2. Plants of the new *Caladium* grew faster than plants of 'Mount Everest'.
3. Leaves of plants of the new *Caladium* were more rounded than and not as narrow as leaves of plants of 'Mount Everest'.
4. Plants of the new *Caladium* and 'Mount Everest' differed in leaf coloration as plants of 'Mount Everest' had white to grey-green-colored leaves with dark pink to red-colored venation and dark green-colored borders.

Plants of the new *Caladium* can be compared to plants of 'White Marble', disclosed in U.S. Plant Pat. No. 18,819. In side-by-side comparisons conducted in Lake Placid, Fla., plants of the new *Caladium* differed primarily from plants of 'White Marble' in the following characteristics:

1. Plants of the new *Caladium* were more compact and denser than plants of 'White Marble'.
2. Plants of the new *Caladium* grew faster than plants of 'White Marble'.

3. Plants of the new *Caladium* and 'White Marble' differed in leaf coloration as plants of 'White Marble' had white-colored leaves with white-colored venation and dark green-colored borders.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new Caladium.

The photograph on the first sheet is a side perspective view of a typical plant of 'White Star' grown in a container in a shadehouse.

The photograph at the top of the second sheet is a side perspective view of typical plants of 'White Star' (top center), 'White Marble' (left) and 'Mount Everest' (right) grown in a shadehouse.

The photograph at the bottom of the second sheet is a side perspective view of typical plants of 'White Star' (top center), 'White Wing' (left) and 'Gingerland' (right) grown in a shadehouse.

The photograph at the top of the third sheet is a top perspective view of typical plants of 'White Star' grown in an outdoor nursery.

The photograph at the bottom of the third sheet is a close-up view of typical freshly-dug tubers and roots of 'White Star'.

The photograph on the fourth sheet is a close-up view of a typical inflorescence of 'White Star'.

DETAILED BOTANICAL DESCRIPTION

The aforementioned photographs and following observations and measurements describe plants grown in 15-cm containers in Avon Park, Fla. during the spring in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 29° C. to 35° C., night temperatures ranged from about 22° C. to 26° C. and light levels were about 8,000 foot-candles (shadehouse) or 10,000 to 12,000 foot-candles (outdoor nursery). Plants had been growing in the shadehouse for nine weeks from planting tubers when the photographs and the detailed description were taken. Plants had been growing in the outdoor nursery for seven months from planting tuber pieces when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Star'.

Parentage:

*Female, or seed, parent.*—*Caladium×hortulanum* 'White Wing', not patented.

*Male, or pollen, parent.*—*Caladium×hortulanum* 'Gingerland', not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to rounded in shape. Height: About 4.2 cm. Diameter: About 6.3 cm. Texture: Thick, starchy; somewhat brittle. Color: Epidermis, close to 199B, with development, close to 200A to 200B; interior, close to 10D. Root description: Dense, thick, fleshy; white, close to 155C, in color.

Plant description:

*Plant type.*—Herbaceous perennial.

*Plant/growth habit.*—Upright and intermediate to tall plant habit; inverted triangle; rapid growth rate; vigorous, dense growth habit; suitable for 15-cm to 25-cm containers. Leaf petioles arising from tubers; petioles mostly upright and leaning and curving outwardly with development.

*Plant height, from soil level to top of leaf plane, shadehouse-grown plants.*—About 30 cm to 39 cm.

*Plant height, from soil level to top of inflorescences, shadehouse-grown plants.*—About 41 cm.

*Plant diameter or spread, shadehouse-grown plants.*—About 52 cm to 58 cm.

*Cataphylls* (*only observed on shadehouse-grown plants*).—Length: About 5 cm to 9 cm. Width: About 1.1 cm. Shape: Lanceolate. Apex: Acute. Base: Sheathing the stem. Color, inner and outer surfaces: Between N170D and 182D with fine streaks, close to 147A and tinged with close to N199B; with development, color becoming closer to between 199C to 200A faintly stained with close to N186D.

Foliage description:

*Length, shadehouse-grown plants.*—About 18.5 cm to 25 cm.

*Width, shadehouse-grown plants* (*flattened*).—About 12 cm to 18 cm.

*Shape.*—Ovate.

*Apex.*—Acuminate.

*Base.*—Sagittate-peltate to sagittate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Close to 191C to 191D; random diffuse areas, close to 147A, 191C, 137A or 155C; basal notch, close to 187A to 187C. Border and margins: Close to 147A; thin edge, close to N186C. Venation: Midrib, close to 155C flushed with close to 49C to 49D; lateral veins, close to 155C flushed with close to 49D. Developing leaves, lower surface: Center: Close to 155C; random diffuse areas, close to 137B, 191A or 147B. Border and margins: Between 137B and 191A often variably and faintly tinged with close to N186C. Venation: Midrib and lateral veins, close to 159C tinged with close to 36C to 36D. Fully expanded leaves, upper surface: Center: Close to 191C; random diffuse areas, close to 147A, 147B, 191C, 137B or 155C occasionally tinged with close to 62D; basal notch, close to 187A to 187B; occasion random spots, close to 60A to 60B. Border and margins: Between 137A and 147A; thin edge, close to N186C. Venation: Midrib and lateral veins, close to 62C to 62D to close to 59B to 59C. Fully expanded leaves, lower surface: Center: Close to 155C tinged with close to 62D; random diffuse areas, close to 191A, 147B to 147C and 137C; random spots, close to 186A to 186B; basal notch, close to 187A to 187C. Border and margins: Close to 191A; fine edge, close to N186C. Venation: Midrib, close to 181D; lateral veins, close to 51D.

*Petiole.*—Aspect: Mostly erect, leaning and curving outwardly with development. Length, shadehouse-grown plants: About 24 to 33.5 cm. Diameter, distal, shadehouse-grown plants: About 3.2 mm to 5 mm. Diameter, proximal, shadehouse-grown plants: About 7 mm to 10 mm. Color, proximal, shadehouse-grown plants: Between 182D and N170D variably and densely streaked and marked with between N199B to 147A. Color, distal, shadehouse-grown plants: Close to 182C to 182D faintly tinged with close to 177D and variably and finely streaked with between N199B and 147A. Wing length, shadehouse-grown plants: About 4.5 cm to 6.7 cm. Wing diameter, shadehouse-grown plants: About 6 mm to 10 mm. Wing color, shadehouse-grown plants: Between N170D and 182D variably streaked with close to 147A and tinged with close to N199B.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about six weeks after growth commences. Inflorescences last about three days before fading; inflorescences persistent.

*Spathe.*—Length: About 13.5 cm. Width, distal: About 3.2 cm. Width, proximal: About 3 cm. Width, at constriction: About 2 cm. Shape: Ovate. Apex: Acuminate. Base: Tapering. Margin: Entire; slightly reflexed. Texture, upper and lower surfaces: Smooth, glabrous. Color: Front surface: Upper two-thirds: Close to 159C to 159D faintly tinged with close to 194B; color becoming closer to 199B to 199C with development. Lower one-third: Between 138B to 143C; towards the base, deeply colored with close to N186C; color becoming closer to between 137C and 147B streaked and mottled with close to 146D and 148D with development. Rear surface: Upper two-thirds: Between 160D and 162C variably tinged with close to 146D. Lower one-third: Between 137C and 147B streaked and mottled with close to 146D and Spadix: Length, entire spadix: About 9 cm. Length, male flower zone: About 6.5 cm. Length, sterile flower zone: About 7 mm. Length, female flower zone: About 2.5 cm. Diameter, male flower zone: About 1.1 cm. Diameter, sterile flower zone: About 9 mm. Diameter, female flower zone: About 1.1 cm. Shape: Spindle-shaped to columnar. Apex: Bluntly acute. Base: Obtuse. Aspect: Upright. Color, mature, male zone: Close to 159D. Color, mature, sterile zone: Close to 159D. Color, mature, female zone: Close to 164D. Male flowers: Quantity per spadix: About 329. Shape: Obovate. Height: About 3.5 mm. Diameter: About 2 mm. Anther color: Close to 159D. Amount of pollen: None observed. Female flowers: Quantity per spadix: About 268. Shape: Obovate. Height: About 3.5 mm. Diameter: About 2.2 mm. Stigma color: Close to 164D. Ovary color: Close to 4D. Scape: Length: About 28.5 cm. Diameter: About 7 mm. Strength: Sturdy; flexible. Aspect: Erect. Texture: Smooth, glabrous; glaucous. Color: Proximal: Close to N170D tinged with close to 182D and streaked with close to 147A tinged with close to N199B. Distal: Between 147B and 191B to 191C. Seed and fruit: Seed and fruit development have not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'White Star' as illustrated and described.

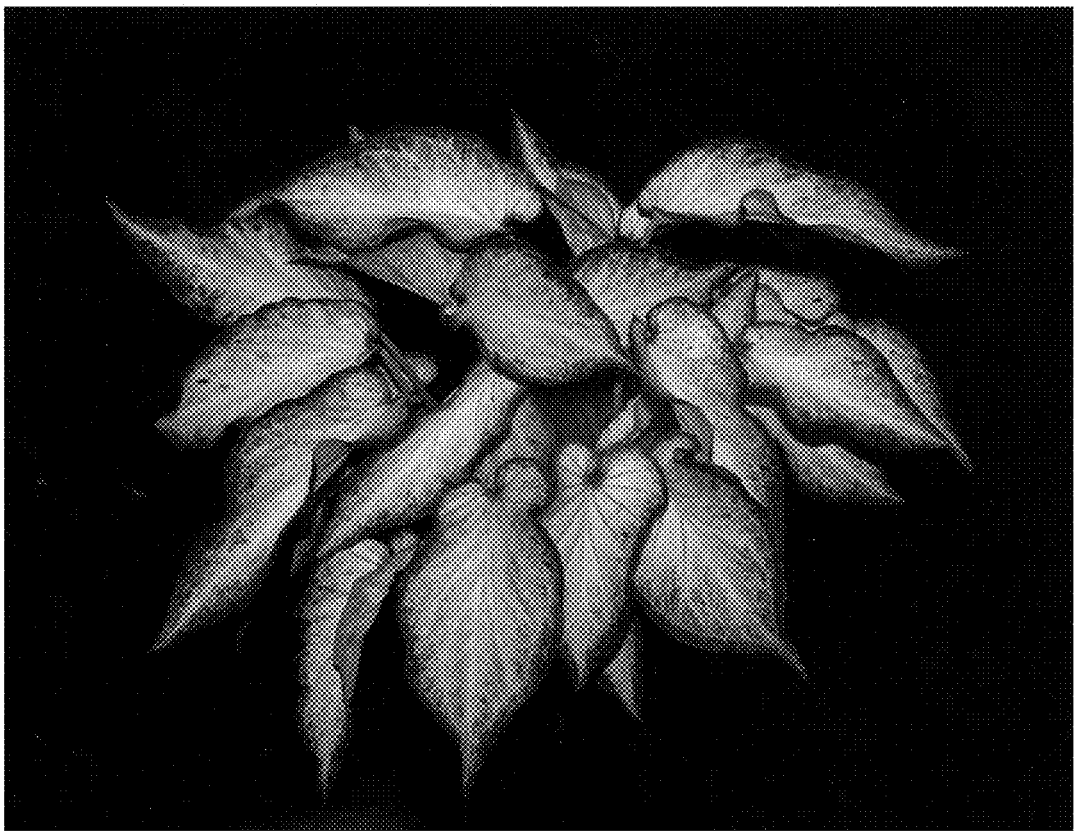

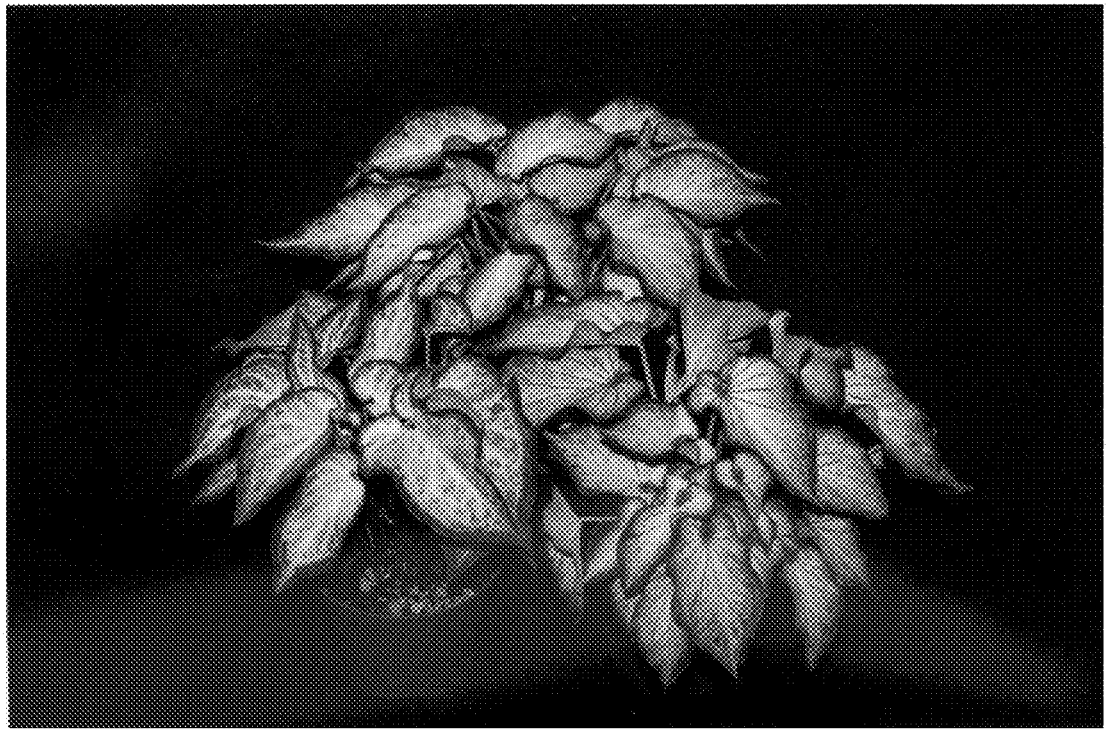
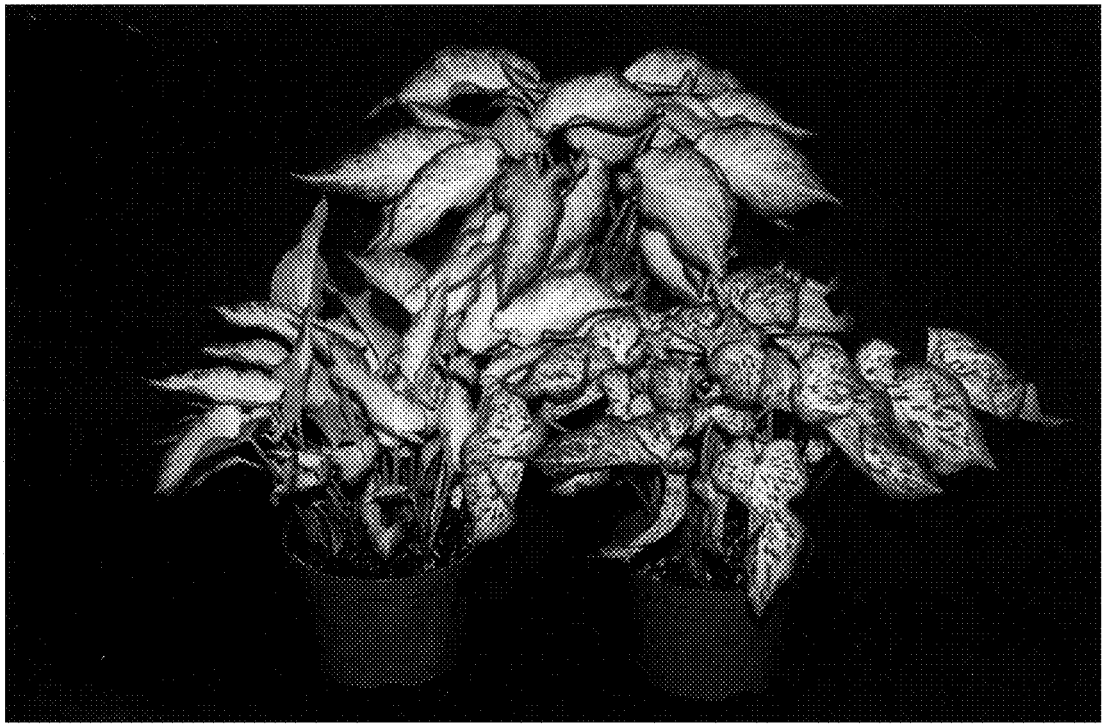

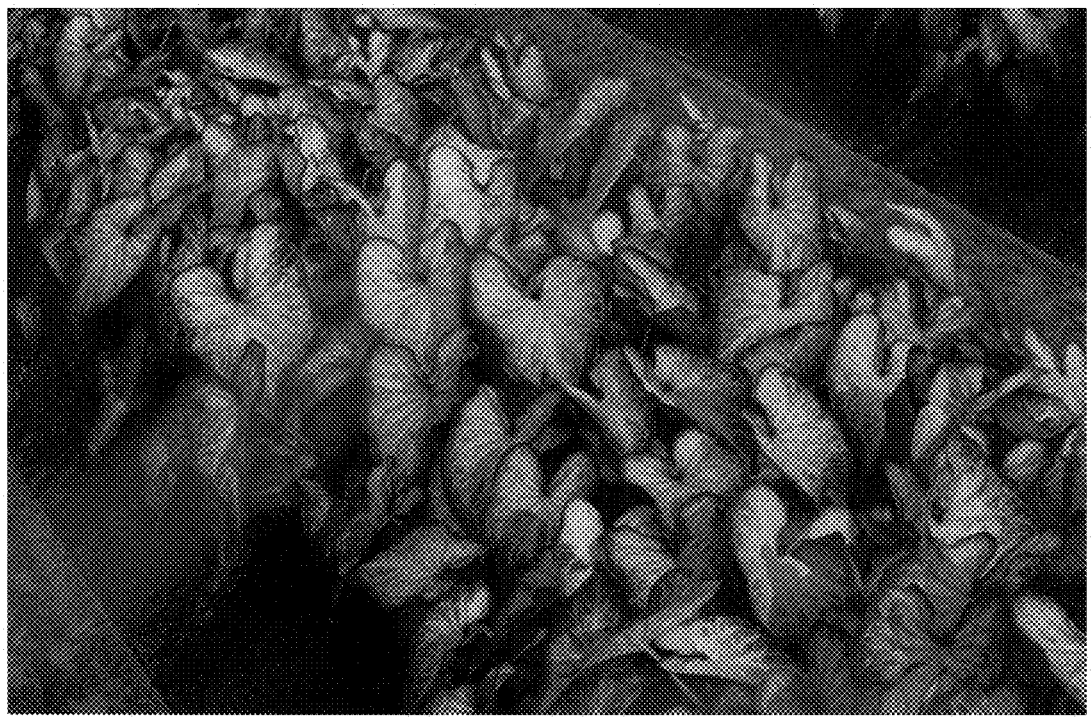
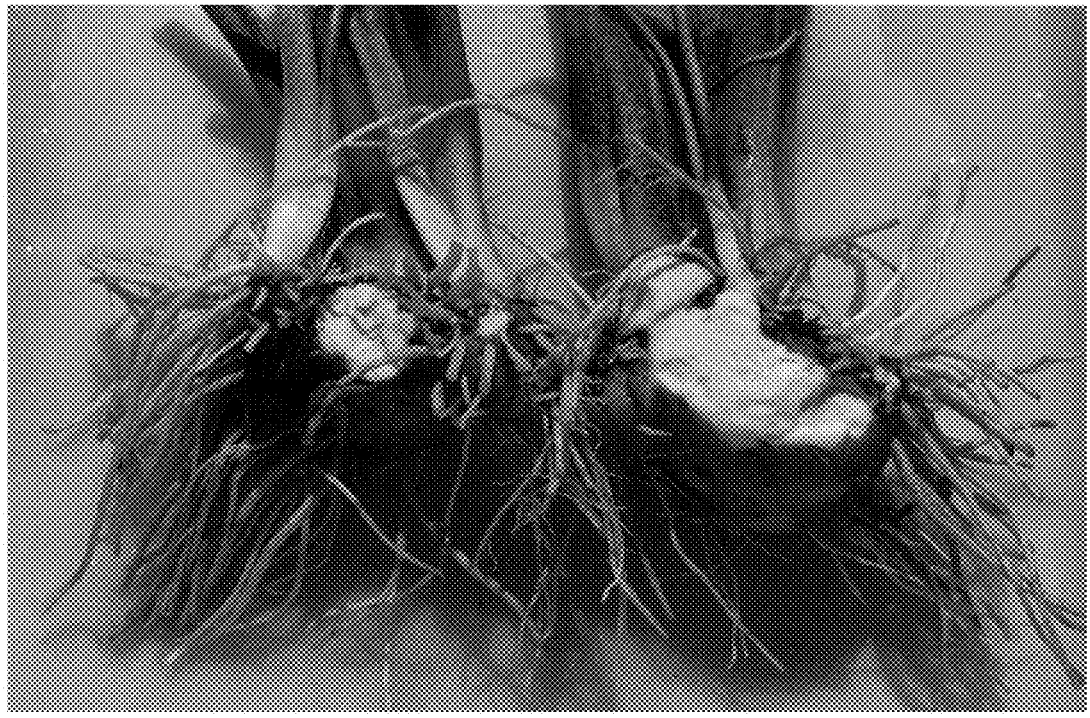

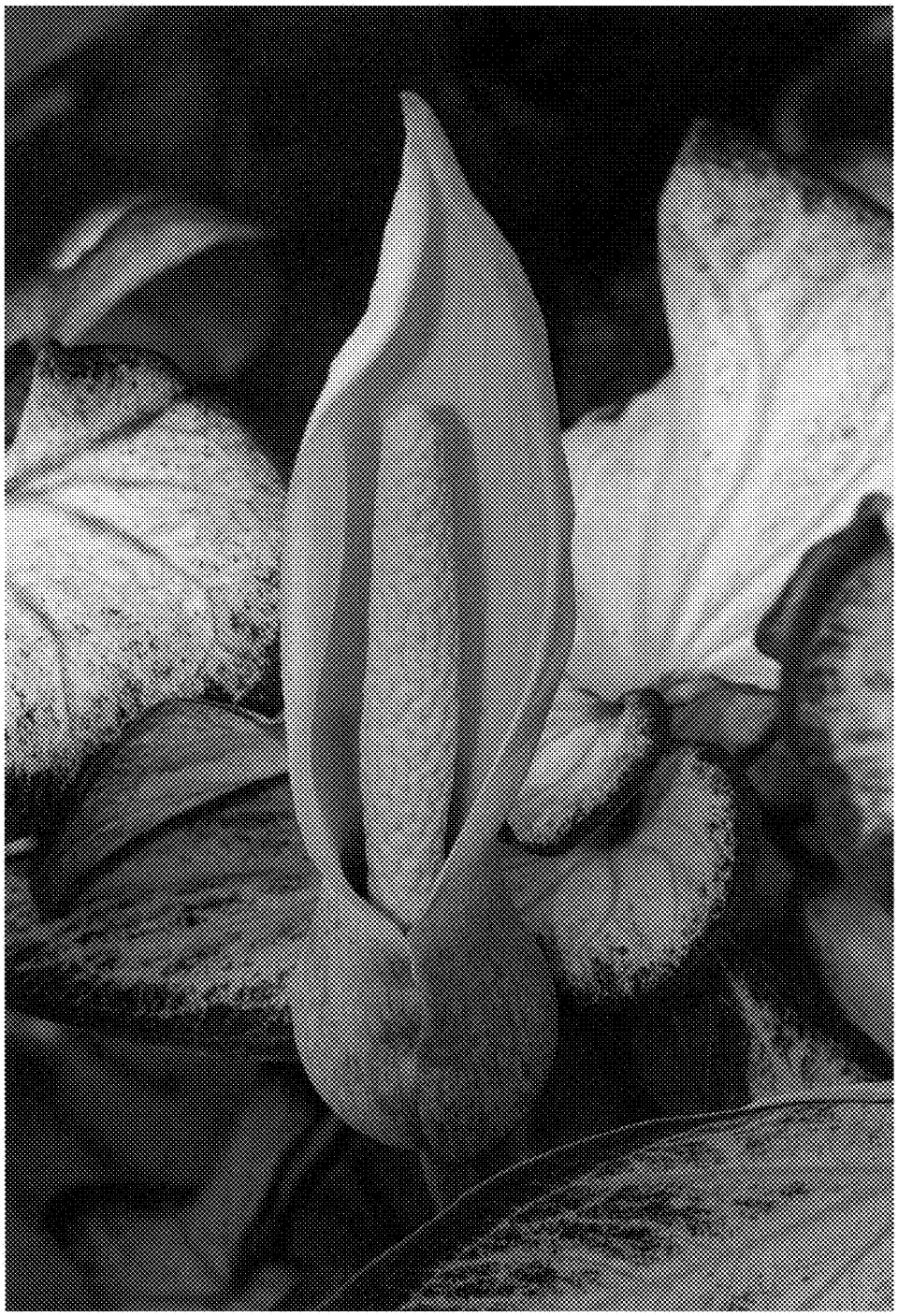

* * * * *